(12) United States Patent
Jun et al.

(10) Patent No.: US 10,111,452 B2
(45) Date of Patent: Oct. 30, 2018

(54) METHOD OF SUPERCOOLING PERISHABLE MATERIALS

(71) Applicant: University of Hawaii, Honolulu, HI (US)

(72) Inventors: Soojin Jun, Honolulu, HI (US); Jin Hong Mok, Honolulu, HI (US); Sung Hee Park, Honolulu, HI (US)

(73) Assignee: UNIVERSITY OF HAWAII, Honolulu, HI (US)

( * ) Notice: Subject to any disclaimer, the term of this patent is extended or adjusted under 35 U.S.C. 154(b) by 118 days.

(21) Appl. No.: 15/102,856

(22) PCT Filed: Dec. 9, 2014

(86) PCT No.: PCT/US2014/069402
§ 371 (c)(1),
(2) Date: Jun. 8, 2016

(87) PCT Pub. No.: WO2015/089112
PCT Pub. Date: Jun. 18, 2015

(65) Prior Publication Data
US 2016/0302457 A1 Oct. 20, 2016

Related U.S. Application Data

(60) Provisional application No. 61/914,270, filed on Dec. 10, 2013.

(51) Int. Cl.
| | |
|---|---|
| *A23L 3/36* | (2006.01) |
| *A23L 3/26* | (2006.01) |
| *A23L 3/32* | (2006.01) |
| *A01N 1/02* | (2006.01) |
| *C12N 13/00* | (2006.01) |

(52) U.S. Cl.
CPC .............. *A23L 3/36* (2013.01); *A01N 1/0252* (2013.01); *A01N 1/0284* (2013.01); *A23L 3/26* (2013.01); *A23L 3/32* (2013.01); *C12N 13/00* (2013.01); *A23V 2002/00* (2013.01)

(58) Field of Classification Search
CPC ..... A23L 3/26; A23L 3/32; A23L 3/36; A23V 2002/00; C12N 13/00
See application file for complete search history.

(56) References Cited

U.S. PATENT DOCUMENTS

| | | |
|---|---|---|
| 2005/0005611 A1 | 1/2005 | Owada |
| 2010/0083687 A1 | 4/2010 | Handa et al. |
| 2010/0116151 A1 | 5/2010 | Singleton et al. |
| 2013/0160467 A1 | 6/2013 | Hall et al. |

FOREIGN PATENT DOCUMENTS

FR        2789604 A1    8/2000

OTHER PUBLICATIONS

International Search Report and Written Opinion dated Mar. 6, 2015 in Application No. PCT/US2014/069402.

*Primary Examiner* — Timothy C Cleveland
(74) *Attorney, Agent, or Firm* — Knobbe, Martens, Olson & Bear, LLP

(57) ABSTRACT

Perishable products, such as food products, can be preserved by cooling to temperatures below their freezing point without ice crystallization. In some embodiments, the perishable product is cooled to temperatures below the freezing point of water while a pulsed electric field and oscillating magnetic field are applied to the product. Apparatus for supercooling perishable products are also provided and include a pulsed electric field generator and an oscillating magnetic field generator.

30 Claims, 14 Drawing Sheets

METHOD OF SUPERCOOLING PERISHABLE MATERIALS

CROSS-REFERENCE TO RELATED APPLICATIONS

The present application is the National Phase Entry of PCT/US2014/069402, which claims priority to U.S. Provisional Patent Application Ser. No. 61/914,270 filed on Dec. 10, 2013, which is herein incorporated by reference in its entirety.

STATEMENT REGARDING FEDERALLY SPONSORED R&D

This invention was made with government support under grant numbers 2009-65503-05786 and 2014-67017-21650 awarded by the National Institute of Food and Agriculture. The government has certain rights in the invention.

BACKGROUND OF THE INVENTION

Field of the Invention

The present application relates generally to the field of preservation of perishable materials, such as food or tissue. Specifically, the present application is directed in some aspects to methods and apparatus for food preservation capable of preserving the freshness of food products while stored at temperatures below the products' freezing point. In other aspects the invention can be applied to storing and preserving other types of perishable materials, such as biological products, including human organs and other tissue.

Description of the Related Art

The preservation of food products is a critical aspect of public health. Among the various methods of food preservation, chilling foods helps to slow the process of decomposition and the growth of contaminating microbial species. Freezing is one of the most effective methods for ensuring the safety of food products and retaining the quality of foods over long storage periods. In spite of its effectiveness, the process of freezing and thawing poses significant problems with respect to the quality of the foods. For instance, during the freezing process ice crystallization and growth can result in irreversible damage to tissue structures in meat, fish, fruit and vegetables, such as structural ruptures and changes in osmotic pressure. Other changes observed to occur in food products during the freezing and thawing process include changes in the food's sensory properties such as color, taste, and freshness. Food products subjected to excessively prolonged freezing may also experience lipid oxidation, protein denaturation, ice recrystallization, and changes in the moisture content. These degrading effects on the quality of food products are directly related to the degree of structural damages to the food products caused by the formation, growth, and distribution of ice crystals within the food products. Such problems associated with freezing food products show the importance of controlling the formation and growth of ice crystals within food products during the storage period.

To overcome these considerable issues, freezing technologies have been developed based on the manipulation of water properties. Most of these developments are aimed at inducing the quick freezing of water by instant nucleation or at controlling the size of ice crystals through the external application of stress. To this end, several studies have examined the supercooling phenomenon under different conditions and treatments. Supercooled solutions under an electric field have also been investigated. However, none of these studies have assessed how to prolong the supercooled state in foods at freezing temperatures and during extensive storage periods.

Methods and apparatus for effectively prolonging the supercooled state in foods and other perishable materials, such as organs harvested for transplantation, would be beneficial and could enable gentler storage and transportation of perishable materials while avoiding many of the problems associated with freezing and thawing.

SUMMARY OF THE INVENTION

Disclosed herein are methods of achieving and maintaining a supercooled state in perishable products. Also disclosed herein, are apparatus capable of supercooling such products according to the methods disclosed herein. These methods and apparatus may be applied to a variety of perishable materials and/or substances, including food products and biological tissues, such as organs.

In some aspects, methods of supercooling a perishable product in a container are provided. The perishable product may be cooled to a temperature in the range of about 0° C. to about −20° C. while applying an oscillating magnetic field to the perishable product. In some embodiments a pulsed electric field is also applied while cooling the product. Once cooled, the oscillating magnetic field and a pulsed electric field are applied to the product. The product may be maintained at the supercooled temperature for a desired period of time. In some embodiments the product may be cooled to about −4° C. to about −7° C. In some embodiments no ice crystals form in the supercooled product.

The pulsed electric field may be provided as a pulsed squared waveform, and may be provided at a frequency of at least 20 kHz. The oscillating magnetic field may have a strength of about 50 to 500 mT, as measured at the center of the container holding the product.

In some embodiments the perishable product may be selected from food products, organs, tissues, biologics, cell cultures, stem cells, embryos, blood, reactive solutions, and unstable chemical reagents. In some embodiments the perishable product remains suitable for its intended purpose after storage at the supercooled temperature.

In some embodiments, methods of preserving a food product at a temperature below the freezing point of the food product are provided. In the methods the food product preferably does not freeze. The food product is cooled to a temperature below its freezing point while applying an oscillating magnetic field. In some embodiments a pulsed electric field is also provided during cooling. The food is maintained at the temperature below its freezing point while applying a combination of the oscillating magnetic field and the pulsed electric field.

In some embodiments the food product comprises meat, such as chicken, beef or fish. Is some embodiments the food product comprises vegetables. The food product may be preserved for 24 hours or more, 72 hours or more, or even more than two weeks.

In some embodiments there is no significant change in one or more of the color, drip loss, or tenderness of the food product relative to food products that were not preserved. In some embodiments, one or more characteristics of the preserved food product are preserved relative to a food product that was frozen.

The pulsed electric field may be provided as a squared waveform. In some embodiments the squared waveform is provided with a duty cycle of about 0.2 to about 0.8. More than one different duty cycle may be provided during the preservation process. For example, duty cycles of 0.2, 0.5 and 0.8 may be provided. The oscillating magnetic field may have a strength of about 50 to 500 mT.

In some embodiments methods of preserving an organ are provided. The organ is supercooled to a temperature below 0° C. while applying an oscillating magnetic field. A pulsed electric field may also be provided during the cooling process in some embodiments. A combination of the oscillating magnetic field and the pulsed electric field are provided to maintain the organ at the supercooled temperature without freezing. In some embodiments the organ is maintained at a temperature below 0° C. for more than 24 hours while continuing to apply the pulsed electric field and oscillating magnetic field. The organ preferably remains viable for its intended use after storage.

In another aspect, apparatus are provided that can be used for supercooling perishable products, such as food, organs and tissue. In some embodiments the apparatus comprises a container for holding one or more perishable products, a pulsed electric field generator and an oscillating magnetic field generator. The pulsed electric field generator comprises at least two electrodes arranged to contact the perishable products when they are placed in the container. The oscillating magnetic field generator is configured to generate an oscillating magnetic field in the container.

In some embodiments the pulsed electric field generator is controlled to provide a pulsed squared waveform. The pulsed electric field generator may, for example, be controlled by an insulated-gate bipolar transistor.

In some embodiments the oscillating magnetic field generator comprises four solenoid coils at each side of the container.

In some embodiments the apparatus is portable, and may be placed into a separate freezing apparatus for cooling. In some embodiments the apparatus is part of a refrigerator or freezer. In some embodiments the apparatus comprises elements to reduce the temperature in the container to a desired temperature, such as in the range of 0° C. to about −20° C.

BRIEF DESCRIPTION OF THE DRAWINGS

FIG. 3A depicts side electrodes (top view) and B) depicts bottom electrodes (top view).

FIG. 7A shows the electric current changes during the freezing process. FIG. 7B shows electrical conductivities of chicken breasts as a function of temperature. The circled portion indicates the changes of electric conductivities during the phase transition.

FIG. 8A shows the square waveform pulsed electric field with duty cycle sequences of 0.8 for 300 seconds, 0.5 for 120 seconds, and 0.2 for 90 seconds. FIG. 8B shows corresponding temperature profiles of chicken breasts with OMF treatment only when the duty cycle of 0.2 is applied.

FIG. 10A shows micrographs for chicken refrigerated at 4° C. FIG. 10B shows micrographs for chicken frozen at −7° C. and FIG. 10C shows micrographs for chicken supercooled by the PEF and OMF combination at −7° C.

DETAILED DESCRIPTION

Improved methods of storage and/or preservation of food products, organs and tissues, and other perishable materials are desired. Disclosed herein are methods of achieving and maintaining a supercooled state in such perishable products. To control supercooling, a combination of pulsed electric field (PEF) and oscillating magnetic field (OMF) can be applied to the perishable materials. It is hypothesized that the combination of pulsed electric field and oscillating magnetic field techniques significantly influence the mobility of water molecules. Using this combination, stable supercooled materials can be obtained through the continuous reorientation and induced vibration of water molecules, thereby suppressing the formation of ice.

In some embodiments, methods of supercooling a perishable product, such as a food product, comprise cooling the perishable product to a temperature below its freezing point while applying a pulsed electric field and oscillating magnetic field to the perishable product. The pulsed electric field and oscillating magnetic field are maintained while the product is stored in the supercooled state. In some embodiments the product does not freeze in the supercooled state. In some embodiments the perishable product is a product that contains water.

Figure 4:
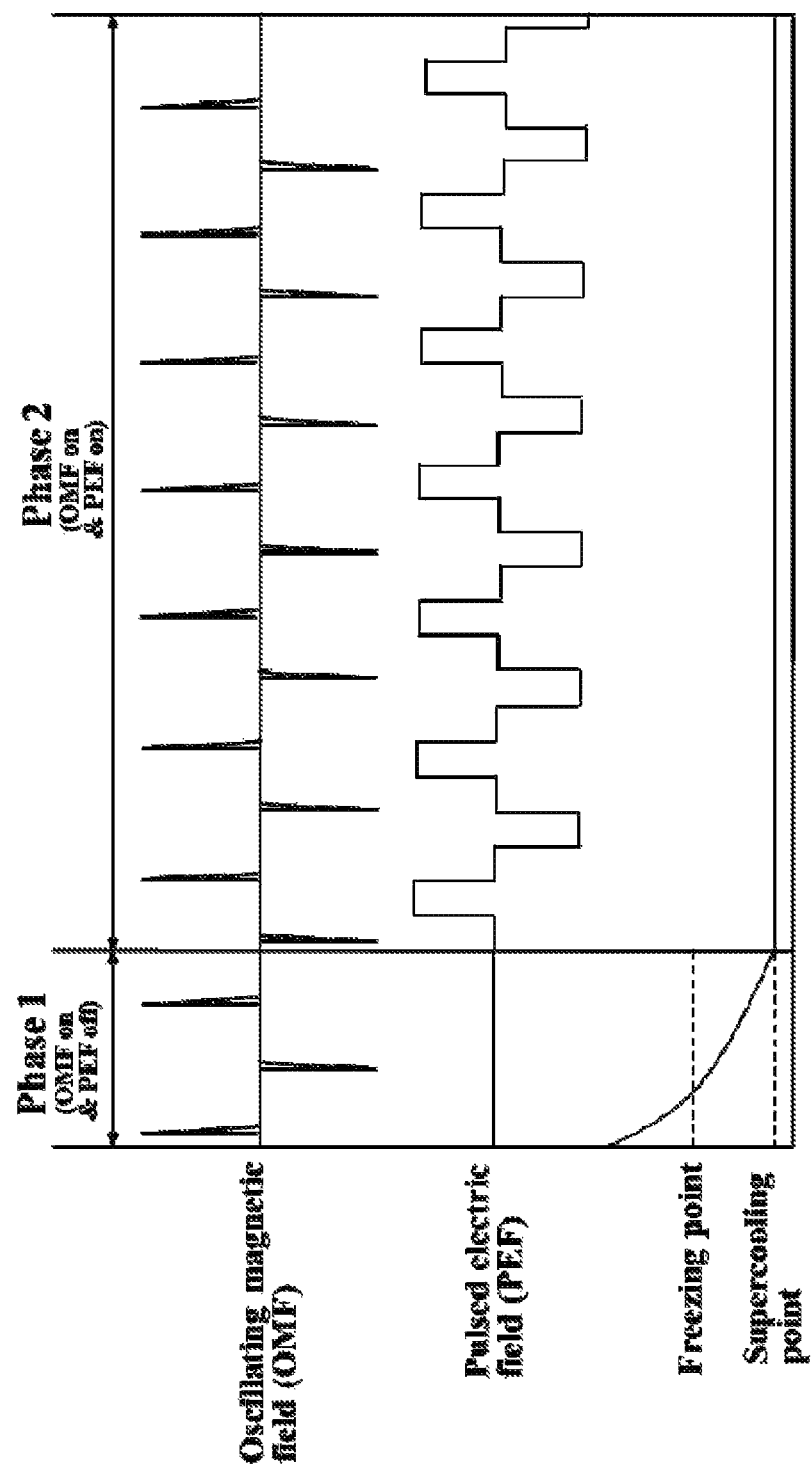
FIG. 4 displays the stepwise control of OMF and PEF during supercooling.

In some embodiments the perishable product is first cooled while applying an oscillating magnetic field. In some embodiments the pulsed electric field is not applied at this time. For example, the product can be supercooled by being placed in an apparatus, as described in more detail below, while an oscillating magnetic field is applied. Once the product has reached a supercool temperature, the pulsed electric field is added and the combination of the pulsed electric field and oscillating magnetic field are maintained for as long as the product is to be stored at a supercooled temperature. The time when the oscillating magnetic field is on and the pulsed electric field is off can be referred to as a first phase, while the time when both the oscillating magnetic field and pulsed electric field are provided can be referred to as a second phase. One such embodiment is illustrated in FIG. 4. In some embodiments the product is cooled while applying the oscillating magnetic field and the pulsed electric field is added when the temperature has stabilized. In some embodiments the product is cooled while applying the oscillating magnetic field and the pulsed electric field is added when a desired temperature has been reached. For example, the pulsed electric field may be added when a temperature at which the product is to be stored has been reached. In some embodiments the temperature may be between about −1° C. and about −20° C., for example about −7° C. or about −8° C. In some embodiments the product is cooled while applying both the oscillating magnetic field and the pulsed electric field, and both are maintained during storage.

The use of the pulsed electric field and the oscillating magnetic field suppresses the nucleation of ice crystals in the perishable product and the product attains a supercooled state without freezing. The pulsed electric field and oscillating magnetic field can be maintained in order to maintain the perishable product at the supercooled state for an extended period of time, thus maintaining the quality of the product.

In some embodiments, the perishable product is cooled to a selected temperature that is less than the freezing temperature of the product. In some embodiments the perishable produce is cooled to a selected temperature that is less than the freezing temperature of water, or 0° C. In some embodiments the selected temperature can be between −1° C. and −20° C. Temperatures in the range of −4° C. and −8° C. are commonly applied in some embodiments.

In some embodiments the pulsed electric field is applied as a squared waveform. In some embodiments, the squared waveform can have a frequency of about 0 to about 100 kHz. In some embodiments the frequency is about 20 kHz or above.

In some embodiments, the squared waveform can be provided with a duty cycle of about 0.1 to about 0.9, more preferably about 0.2 to about 0.8. In some embodiments a duty cycle of 0.2, 0.5 or 0.8 is used. In some embodiments a duty cycle of 0.5 is used.

In some embodiments, more than one duty cycle can be used during application of a pulsed electric field to a product. In some embodiments a mixed sequence of duty cycles is used. For example, in some embodiments duty cycles of 0.2, 0.5, and 0.8 are used.

When more than one duty cycle is used, each duty cycle is carried out for a desired length of time. In some embodiments, one or more duty cycles may be applied for a time of from about 1 to about 1000 seconds or more. In some embodiments one or more duty cycles may be applied for about 50 to 500 seconds. In some embodiments one or more duty cycles are applied for 90 seconds. In some embodiments one or more duty cycles are applied for 120 seconds. In some embodiments one or more duty cycles are applied for about 300 seconds.

In some embodiments one or more duty cycles are applied for the same length of time. For example, each duty cycle may be carried out for the same length of time throughout the time that the PEF is provided. In some embodiments each duty cycle is carried out for a different length of time.

A sequence of duty cycles applied for particular lengths of time may also be repeated one or more times during application of the PEF. In some embodiments a PEF with a duty cycle sequence of 0.8, 0.5 and 0.2 is applied for 300 sec, 120 sec, and 90 sec. respectively, to a perishable material. The sequence may be repeated to maintain the perishable material in a supercooled state. In some embodiments a duty cycle sequence suitable for supercooling and maintaining a supercooled state in water-containing perishable materials follows the sequence 0.8 for a period of 300 seconds, 0.5 for a period of 120 seconds and 0.2 for a period of 120 seconds.

In some embodiments, the pulsed electric field has a strength of about 0.6 V/cm to about 10 V/cm.

In some embodiments, the oscillating magnetic field has a strength of about 50 to 500 milliTesla as measured at the center of the chamber holding the perishable product. In some embodiments the oscillating magnetic field has a strength of about 50 to about 150 mT at the center of the chamber.

The methods described herein may impede ice crystal formation. In some embodiments the perishable product does not freeze during supercooling or while maintained in a supercooled state. In some embodiments the perishable product is less frozen than the same type of product maintained at the same temperature for the same amount of time, but that is not subjected to PEF and OMF as described herein. In some embodiments, no ice crystals are formed within the supercooled perishable product. In some embodiments finer ice crystals are formed in the perishable product than are formed in the same type of perishable product under similar conditions without the application of both of the pulsed electric field and oscillating magnetic field. In some embodiments any ice crystals that may form do not negatively affect the sensory properties and/or intended use of the perishable product.

In some embodiments the perishable product is maintained in a supercooled state for at least 24 hours while continuing to apply the pulsed electric field and oscillating magnetic field. In some embodiments the perishable product is maintained in a supercooled state for at least 72 hours while continuing to apply the pulsed electric field and oscillating magnetic field. In some embodiments the perishable product is maintained in a supercooled state for at least two weeks while continuing to apply the pulsed electric field and oscillating magnetic field. In some embodiments the perishable product is maintained in a supercooled state for a month or more. In some embodiments the perishable product does not freeze during the time that it is maintained in the supercooled state.

As mentioned above, the methods described herein can be applied to the preservation of food products by maintaining them in a supercooled state. Thus, in some embodiments, methods of maintaining a food product in a supercooled state comprise supercooling a food product by cooling the food product to a temperature range below its freezing point, such as to about 0° C. to about −20° C., or about −4° C. to about −7° C., while applying an oscillating magnetic field and, in some embodiments a pulsed electric field, to the food product as described above. The temperature of the food product may be maintained within the range of about −4° C. to about −7° C. while applying the combined pulsed electric field and oscillating magnetic field to the food product. In some embodiments the temperature is maintained for at least 24 hours, or at least 72 hours. In some embodiments the temperature is maintained for two weeks or more.

In some embodiments a food product is preserved such that its qualities do not significantly change from a fresh product. For example, in some embodiments the drip loss from a piece of meat that has been preserved using the described methods is not significantly different from the drip loss in a fresh piece of the meat. Similarly, in some embodiments there is no significant change in tenderness in the food, such as a piece of meat, after the supercooling process.

That is, there is not a significant difference between the tenderness a piece of meat or other food that has been treated as described and a fresh piece of the same meat or food. In some embodiments no structural differences are observable between a fresh piece of food and a piece of the same food that has been preserved as described. In some embodiments there is no change in color between food (or other product) that has been preserved as described relative to a fresh piece of the same food (or other product).

In addition, the methods described herein can be used to preserve organs or other tissues after harvest and prior to transplantation or other use. The organs or tissues may come, for example, from a human or animal. In some embodiments the organ is a human organ to be used for transplantation. In this way the quality of the organs or tissues can be maintained during transport, storage and preparation. In some embodiments, methods of maintaining an organ or other tissue in a supercooled state comprise supercooling the organ or tissue by cooling to a temperature below its freezing point, such as in a range of about 0° C. to about −20° C., or about −4° C. to about −7° C., while applying an oscillating magnetic field (and in some embodiments a pulsed electric field) to the organ or tissue, essentially as described above. The temperature of the organ or tissue may be maintained within the range of about −4° C. to about −7° C. for an extended time while applying both the pulsed electric field and oscillating magnetic field to the organ or tissue. In some embodiments the temperature is maintained for at least 24 hours, or at least 72 hours. In some embodiments the temperature is maintained for two weeks or more. Preferably the organ or tissue remains viable for its intended use throughout the time that it is maintained in a supercooled state.

In some embodiments the methods may be used to preserve other types of materials such as biologics, cell cultures, stem cells, embryos, blood, reactive solutions, and unstable chemical reagents.

In some embodiments, apparatus that can be used to implement the above-described methods for supercooling perishable products are provided. The apparatus typically comprise a container capable of storing one or more perishable products; one or more pulsed electric field generators comprising electrodes positioned to contact the one or more perishable products when they are placed in the container, and one or more oscillating magnetic field generators arranged to form an oscillating magnetic field within the interior of the container. Various embodiments of such apparatus are described in more detail below.

In some embodiments, a refrigerator or other refrigeration or freezing apparatus comprises an apparatus for supercooling food products as described herein (a supercooling apparatus). For example, the apparatus may be provided as a drawer or compartment within a refrigerator or freezer.

In some embodiments, an apparatus for supercooling organs comprises a container capable of storing one or more organs; a pulsed electric field generator comprising electrodes arranged to contact the one or more organs and inducing an electric field therein; and an oscillating magnetic field generator capable of forming an oscillating magnetic field within the interior of the container. The apparatus may be part of a larger refrigerator or freezer, or other apparatus. In some embodiments the apparatus is portable and may be placed in a larger refrigerator or freezer for cooling. In some embodiments the apparatus is portable and comprises cooling elements as well as the supercooling components.

Supercooling

The phenomenon of supercooling may be understood in the context of the ice crystallization process. Ice crystallization can be divided into three subsequent stages; cooling the liquid-state product to its freezing point, removing the latent heat of crystallization during the phase transition, and cooling the solid-state product to the final storage temperature. In a supercooling process, water cools below the freezing temperature until a critical nucleation point is reached by the removal of sensible heat. Ice nucleation is a stochastic process. The negative difference between the temperature at this nucleation point and the standard freezing point is referred to as the degree of supercooling. Depending on the physical conditions of the system, i.e., pressure, temperature, volume, and cooling rate after a certain degree of supercooling, a sudden nucleation of water crystals occurs. Thereafter, the ice crystals become more compact and undergo crystallization to bulk ice crystals.

Figure 1A:
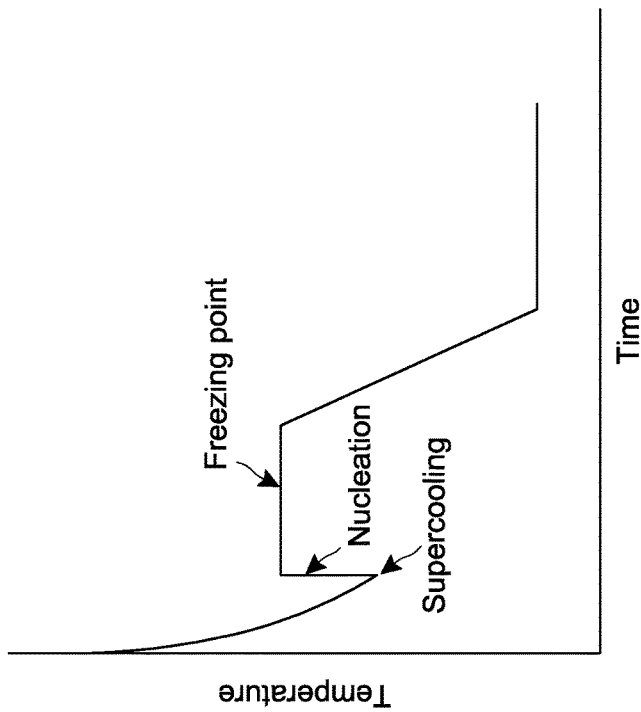
FIGS. 1A and 1B illustrate the expected temperature profile over time in (A) the normal freezing process and (B) when a supercooled state is attained and prolonged.
Figure 1B:
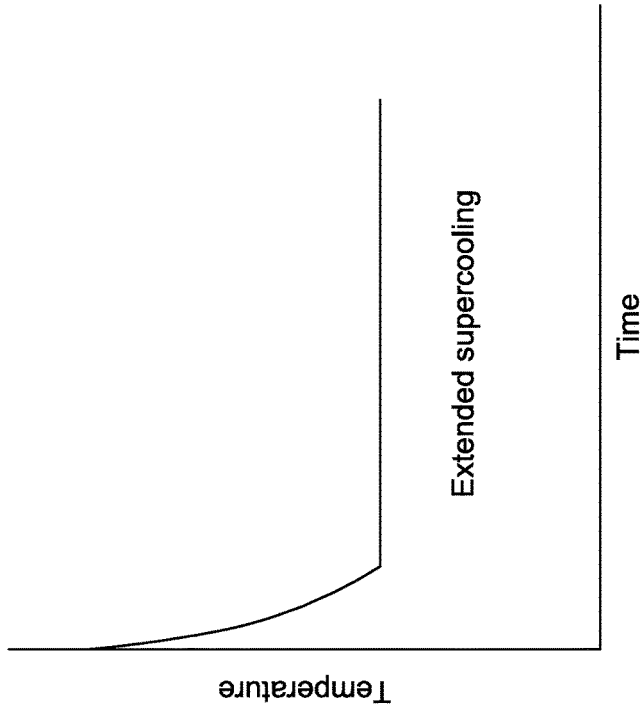

FIG. 1 depicts the difference between bulk ice crystallization and a prolonged supercooled state. FIG. 1A shows the temperature profile of a control in which an initial cooling brings the control to subzero temperature which is quickly followed by nucleation, which is indicated by a sudden increase in temperature. Transformation to the solid crystal form is an isothermal process at the freezing temperature. Once crystallization is complete the ice sample cools until its temperature reaches an equilibrium with its surroundings. In contrast, FIG. 1B shows a sample that is preserved in the supercooled state as described herein. The temperature profile shows that the sample cools to sub-freezing temperatures, but instead of the nucleation of ice crystals occurring, the sample remains at the sub-freezing temperature in the liquid state.

By preventing water molecules from forming a cluster of a critical size that results in ice nucleation, a water-containing material can be maintained in the supercooled state, thus impeding a phase transition to its frozen state. Alternatively, the formation of ice crystals within the material can be controlled, only allowing small ice crystals which do not damage the perishable material. Due to the dipole structure of water molecules, an electric field can be applied to a water-containing material and the types of waveform, frequency, interpulse duration (duty ratio) and field strength of an electric field can be modified to control the discharge and realignment of water molecules along the direction of the electric field. Similarly, due to its diamagnetic properties, magnetic fields make an impact on the intermolecular structure of water.

Cooling of samples in the present methods can be carried out in any of a variety of refrigerators or freezers. In some embodiments a supercooling apparatus is part of a refrigerator, freezer or other cooling device. For example, the supercooling apparatus may take the form of a drawer or compartment in a refrigerator, freezer or other cooling device. In some embodiments a supercooling apparatus is placed into a refrigerator, freezer or other cooling device.

Commercial refrigerators and freezers are available and equipped with variable temperature control enabling the selection of a desired temperature. A non-limiting example of a suitable commercial freezer is a General Electric chest freezer FCM7SUWW (GE, Inc., Fairfield, Conn.).

Digital and analog temperature controllers are available to select the temperature. A suitable non-limiting example of a temperature controller is the Johnson Controls, Inc., A419 digital temperature controller (Milwaukee, Wis.).

Other methods of cooling that may be used include the use of cryogenic liquids (e.g., $N_2$) and solid carbon dioxide (dry ice). Other methods of cooling the perishable materials will be apparent to the skilled artisan.

Pulsed Electric Fields

Pulsed electric fields are created through rapid discharge of electrical energy within a finite period of time. Such pulses follow a pattern known as a waveform, which represents how an electrical current varies over time. Common waveforms for electrical currents include the square wave, the sine wave, the ramp, the sawtooth wave, and the triangular wave. In a squared waveform, the amplitude of the wave alternates at a steady frequency between fixed minimum and maximum values, with the same duration at minimum and maximum. As described elsewhere, in some embodiments a squared waveform is used in applying a PEF to a perishable product.

In addition to having a waveform, pulsed electric fields can follow a duty cycle, as discussed briefly above. A duty cycle is the fraction of time within a given period in which a signal is active. Thus, duty cycle values range between 0 and 1. A duty cycle is expressed by the relationship $D=t/P$, where D is the duty cycle, t is the time the signal is active, and P is the total period over which the signal is delivered. Duty cycles can be programmed to deliver a desired amount of electrical energy in packets over a given period of time. Such duty cycles can further be programmed to follow a sequence in which D and P are varied as the sequence progresses. A non-limiting example of a duty cycle sequence suitable for supercooling and maintaining a supercooled state in water-containing perishable materials follows the sequence 0.8 for a period of 300 seconds, 0.5 for a period of 120 seconds, and 0.2 for a period of 90 seconds. Another non-limiting example of a duty cycle sequence suitable for supercooling and maintaining a supercooled state in water-containing perishable materials follows the sequence 0.8 for a period of 300 seconds, 0.5 for a period of 120 seconds, and 0.2 for a period of 120 seconds. The sequence can be repeated for a defined duration of time or indefinitely.

Power supplies used for generating pulsed electric fields are well known in the art and are commercially available. The power supply can be a capacitor charging power supply with high frequency alternating current (AC). A non-limiting example of a suitable power supply is an integrated-gate-bipolar-transistor based power supply (IGBT), such as IRAMX20UP60A, available from International Rectifier, El Segundo, Calif.

Figure 3A:
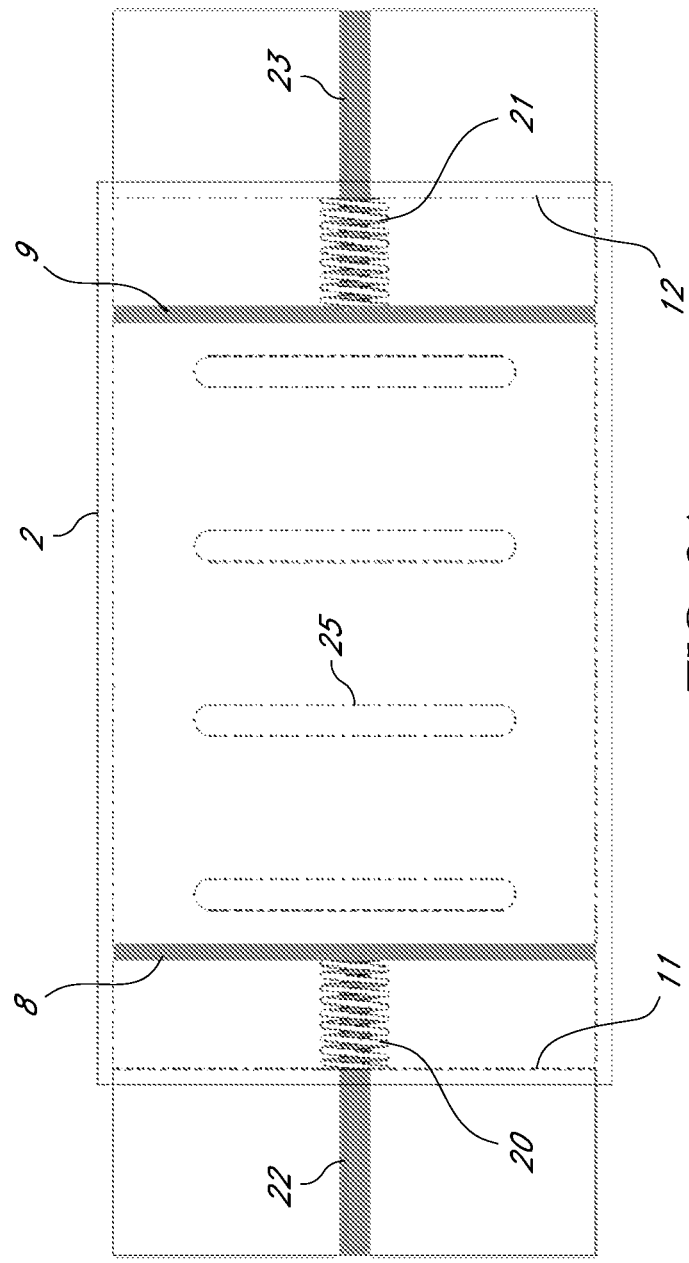
FIGS. 3A and B depict a supercooling compartment portion of an apparatus with various configurations of contact electrodes according to some embodiments.
Figure 3B:
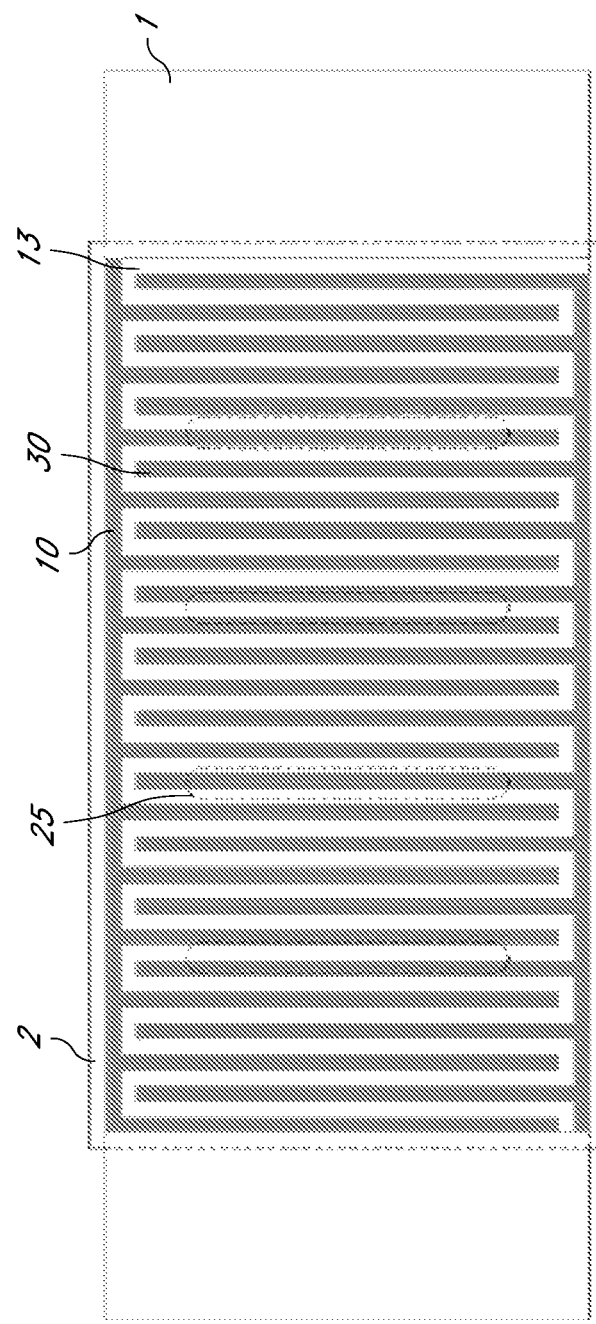

Electrodes coupled to the power supply are placed such that they are directly in contact with the perishable material when it is placed in the container. Suitable electrode materials include, but are not limited to stainless steel, titanium, gold, and silver. The electrodes can be formed in a variety of shapes, including but not limited to plates, prongs, and conductive films. The electrodes can further be designed with multiple holes to enhance the circulation of cold air. Exemplary electrodes are illustrated in FIG. 3. Depending, for example, on the type of food or other perishable material, different types of electrodes can be selected, such as the side electrodes illustrated in FIG. 3A or the bottom electrodes illustrated in FIG. 3B.

The power supply can provide an input voltage. A suitable, non-limiting peak-to-peak voltage setting is about 5 V. Suitable, non-limiting electrical currents provided by the power supply can be up to about 0.04 A. The current produced by the power supply can also be characterized by a working frequency. A suitable, non-limiting example of a frequency for pulsed electric fields applied to supercooling is 20 kHz.

Pulsed electric fields can be controlled using function generators. Suitable function generators are commercially available and well-known in the art. A non-limiting example of a suitable function generator is the Agilent Technologies 33220A (Santa Clara, Calif.). Function generators control square wave forms with various duty cycles and working frequencies.

Oscillating Magnetic Fields

An oscillating magnetic field can be applied to a perishable material as described herein. The oscillating magnetic field may be generated, for example, by using one or more electromagnets or by a combination of an electromagnet with a permanent magnet. A non-limiting example of a suitable permanent magnet is a NdFeB permanent magnet available commercially (N52, DX88-N52, K & J Magnetics, Inc. Jamison, Pa.). A non-limiting example of a suitable electromagnet functions by alternating the charge and discharge to a magnet wire (e.g., 22 AWG, EIS, Inc., Atlanta, Ga.) coiled to an iron core (e.g., VIMVAR, Ed Fagan, Inc., Franklin Lakes, N.J.). Examples of suitable systems for producing an oscillating magnetic field include, but are not limited to, one electromagnet located to one side of the perishable material, two electromagnets located on opposite sides of a perishable material, or an electromagnet and a permanent magnet located on opposite sides of a perishable material. In some embodiments more than one set of electromagnets may be utilized. For example, in some embodiments four electromagnets are located at each side of the container holding the perishable material.

Like the pulsed electric field, a pulsed magnetic field can be generated with a function generator and power supply to the electromagnet. Suitable power supplies are commercially available, and may be, for example, an IGBT as described above. The oscillating magnetic field is regulated via the function generator through an input voltage, which can range from 50 to 150 V at a frequency of 1 Hz. A suitable, non-limiting example of an oscillating magnetic field is a pulse type field with an intensity ranging from −150 mT to 150 mT. Another non-limiting example includes a combined magnetic flux density by permanent magnet and electromagnet oscillated between 50 to 500 mT per second. A person of ordinary skill in the art will recognize that the magnetic field intensity referred to herein is the intensity as measured at the center of the storage container.

Apparatus for Supercooling Perishable Materials

Apparatus for supercooling perishable materials can be used to preserve perishable materials without significant ice crystallization at temperatures below their respective freezing points.

Figure 2A:
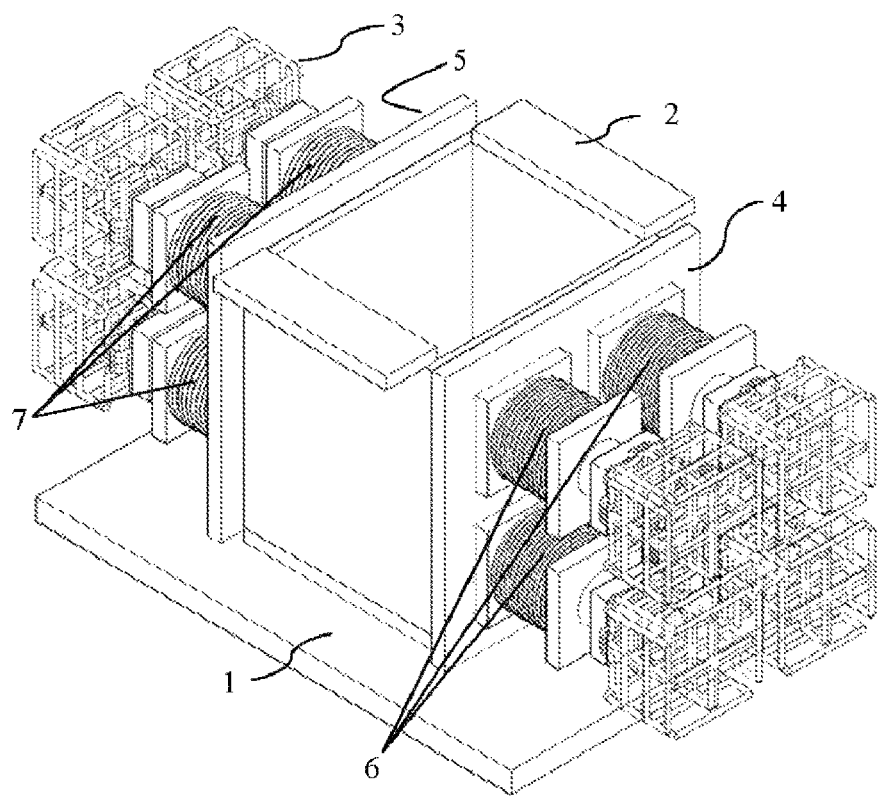
FIGS. 2A-C show embodiments of an apparatus for supercooling perishable materials.
Figure 2B:
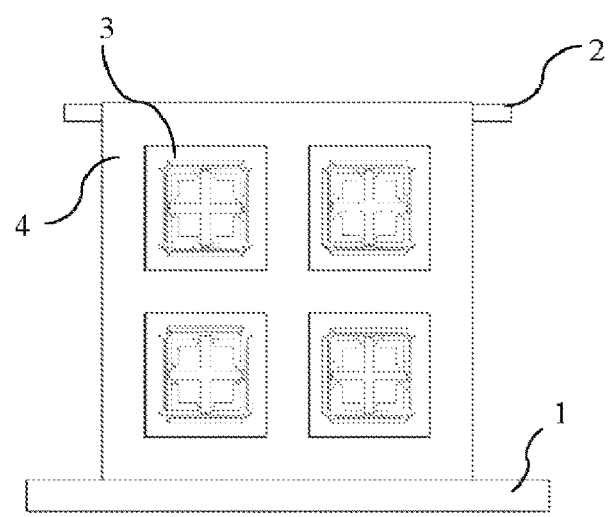
Figure 2C:
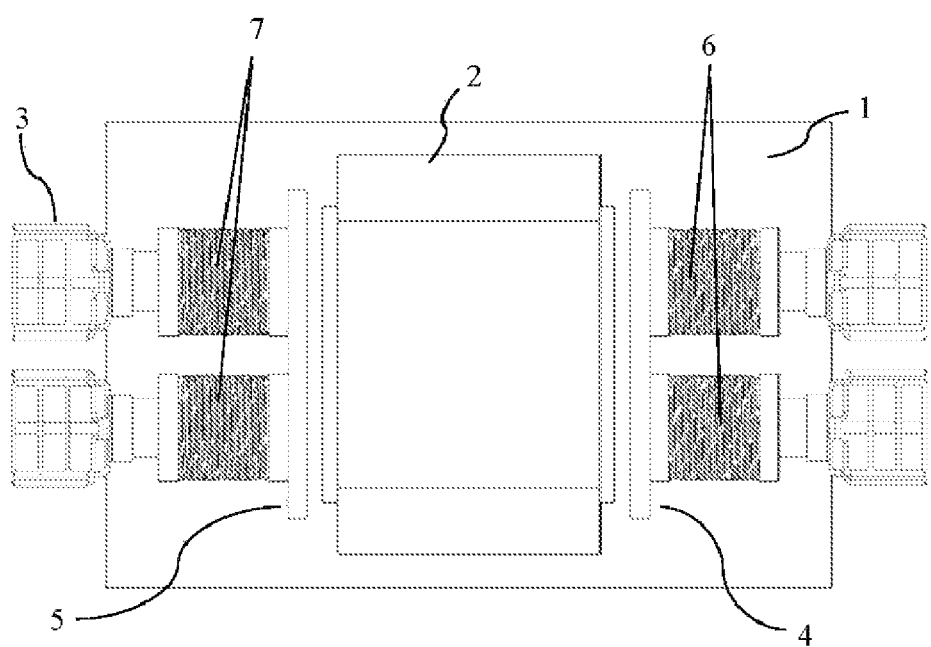

FIGS. 2A-C show three dimensional view illustrating a non-limiting embodiment of an apparatus 1 for supercooling. The apparatus 1 comprises a supercooling compartment 2, in which one or more perishable materials can be placed for supercooling and storage in a prolonged supercooled state. The size of the cooling compartment can be selected depending on the type and size of the perishable material to be treated. An oscillating magnetic field (OMF) generator comprises solenoid coils 6, 7 with attached heat sink 3 located on opposing exterior faces 4 and 5 of the supercooling compartment 2, and can create an oscillating magnetic field with a defined intensity as measured at the center of the cooling compartment. The OMF is generated from the solenoid coils 6 and 7 respectively located on the opposite faces 4 and 5. In some embodiments the apparatus comprises a controller (not shown) for controlling the OMG generator. In some embodiments the controls are set to generate an OMF in the container 2 in the range of 50 to 500 mT. The OMF is regulated through input voltage. In some embodiments the input voltage ranges from 50 to 150 V at 1 Hz frequency. In some embodiments the OMF strength measured at the center of the cooling compartment 2 ranges from 50-500 mT.

The apparatus 1 further comprises a pulsed electric field (PEF) generator which is used to apply the PEF to the perishable material. FIGS. 3A and B shows embodiments of electrodes that can be used to contact the perishable material. The perishable material is placed in cooling compartment 2 and contacted with electrodes 8 and 9. Springs 20 and 21 and side electrode supporters 22 and 23 can be used to maintain contact with the perishable material in the compartment 2. In one embodiment depicted by FIG. 3A, contact electrodes 8 and 9 are respectively located on opposing interior faces 11 and 12 of the container 2. In another embodiment depicted in FIG. 3B, patterned contact electrodes 10, 30 are located on the interior bottom face 13. Vent holes 25 may be provided in one or more faces of the container 2.

The apparatus comprises a controller to control the PEF generator. In some embodiments the controller is set to deliver an applied PEF as a squared waveform, as described herein. An example of an applied PEF delivered as a squared waveform at high frequency (20 Hz) with a programmed duty cycle is shown in FIG. 4. In this non-limiting example, the cooling decays from an initial food temperature to a supercooling temperature during Phase 1 with oscillating magnetic field (OMF) on and PEF off. In Phase 2 (immediately after supercooling is reached), both OMF and PEF applied with programmed duty cycles are used to maintain the supercooling temperature of the food product.

Figure 5:
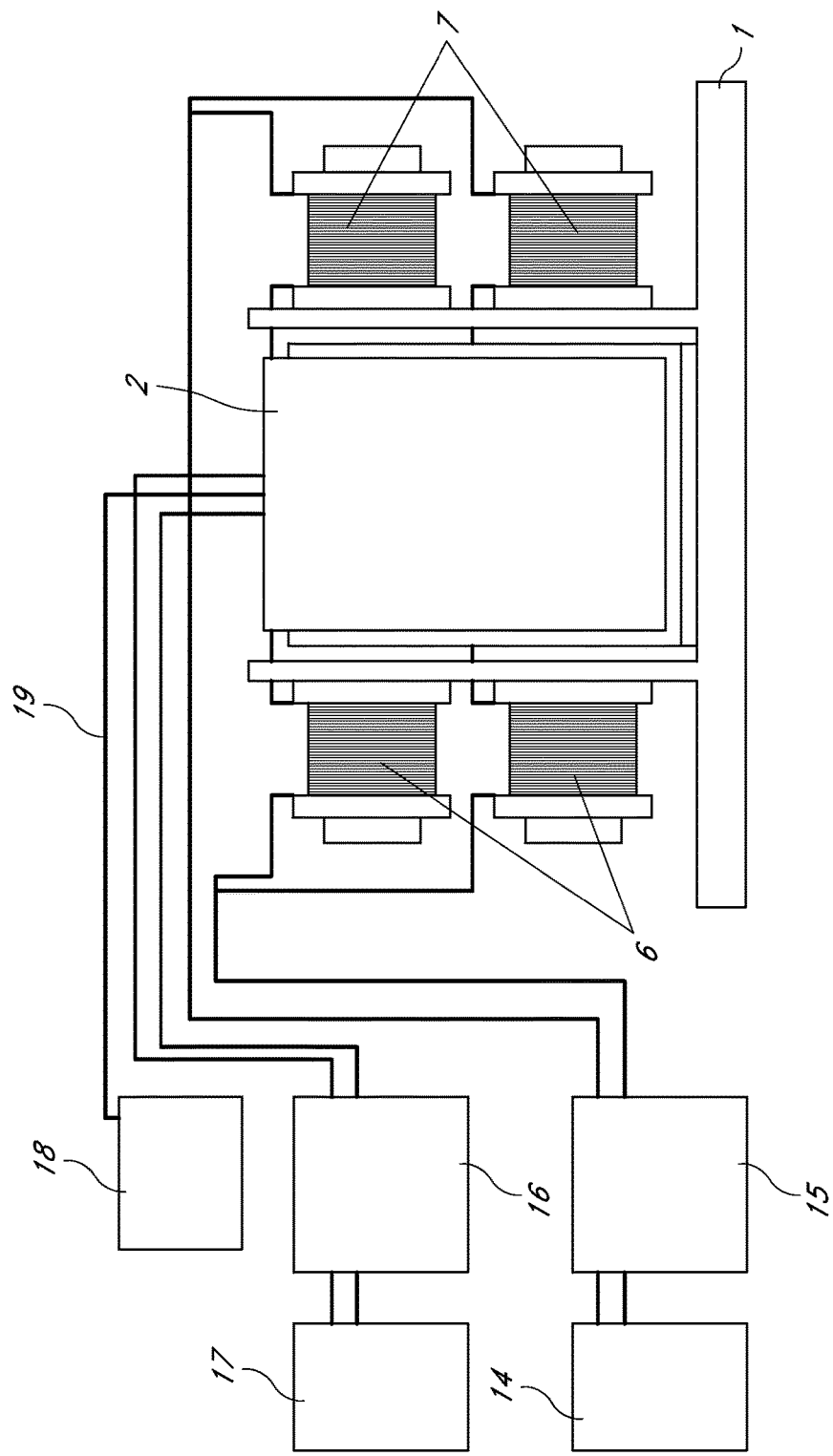
FIG. 5 displays a schematic view illustrating an embodiment of an apparatus for use in supercooling perishable goods.

FIG. 5 shows an embodiment of a schematic view of apparatus 1. Variable transformer 14 coupled with an insulated-gate bipolar transistor (IGBT) power supply for OMF 15 provides the power supply to solenoid coils 6 and 7 thereby generating an oscillating magnetic field in the center of cooling compartment 2. Likewise IGBT 16 coupled with variable transformer 17 provides the PEF to the perishable material via contact electrodes (not shown). Measurements of temperature and electric field strength may be acquired through a Data Acquisition System (DAQ) 18 via thermocouple 19.

A supercooling apparatus as described herein can be included as part of a commercial refrigeration or freezing unit. For example, it may be a built-in part of a refrigeration or freezing unit. In such a configuration, the apparatus can serve as a supercooling storage compartment. In some embodiments the supercooling storage compartment may be removable. In some embodiments, the apparatus can be manufactured independently. For example, the apparatus can be portable and can be placed into a refrigeration or freezing unit. The freezer can be set to the desired temperature to begin the supercooling process.

EXAMPLES

Example 1

Prolonging the Supercooled State in Chicken 1.1 Experimental Procedure

Fresh chicken breast samples were trimmed of all visible connective tissue and excess fat and cut into 1.5 inch by 1.5 inch by 0.75 inch cubic blocks. All samples were weighed and wrapped in polyethylene (PE) film to avoid superficial dehydration before experiments.

Figure 6A:
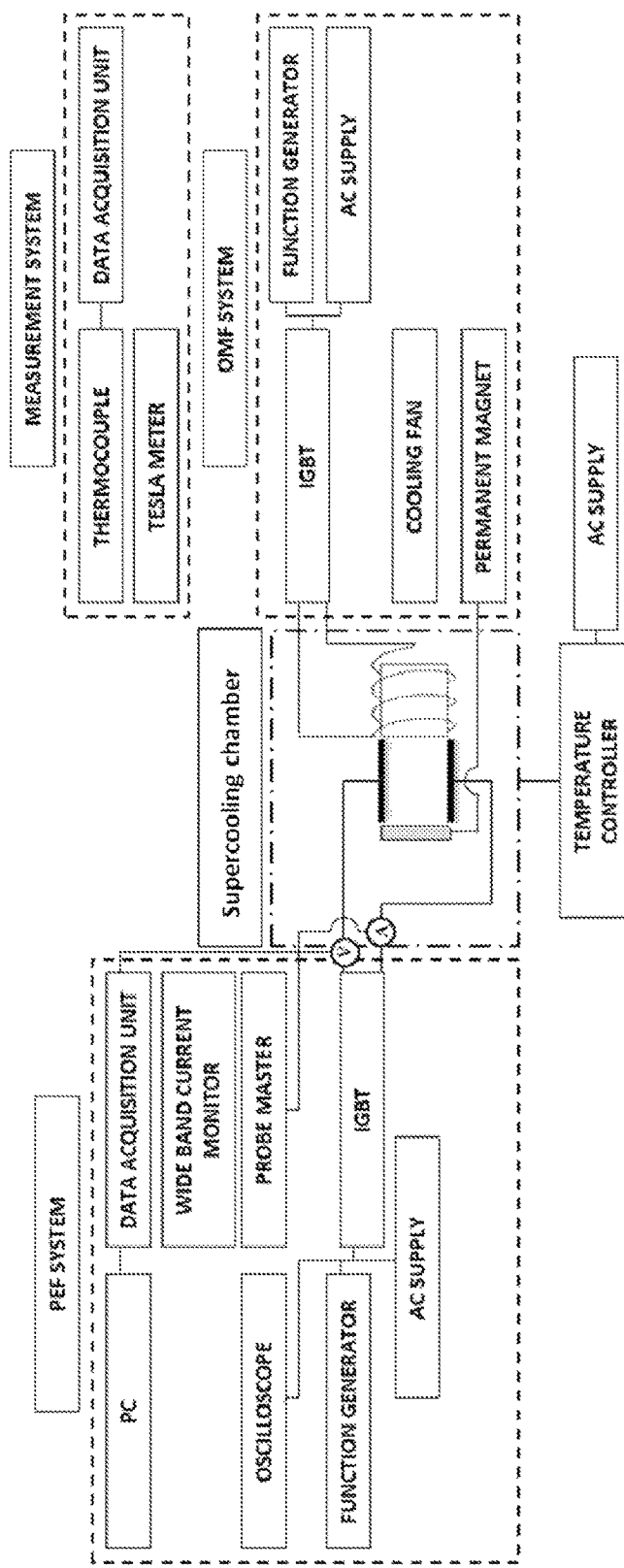
FIG. 6A shows the schematic diagram of an apparatus according to some embodiments that was used in the experiments of Example 1.
Figure 6B:
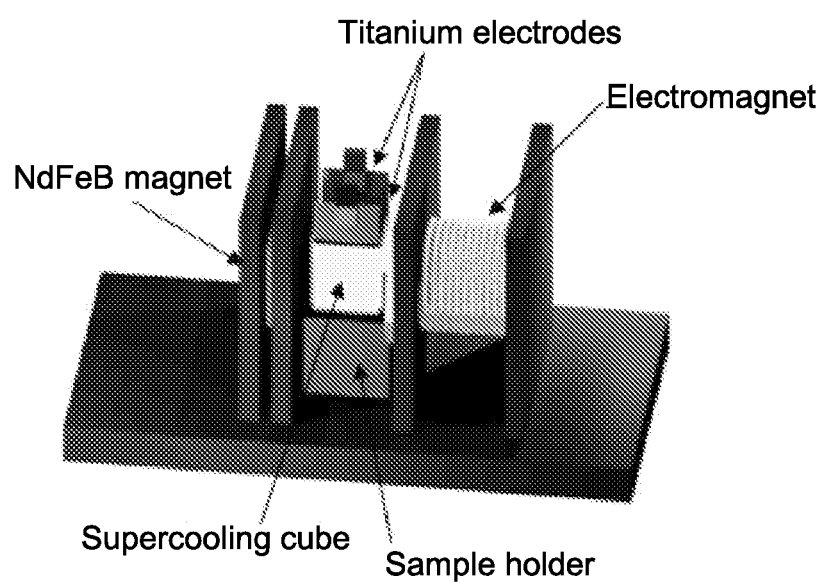
FIG. 6B provides a three dimensional view of a supercooling cube apparatus with the PEF and OMF system that can be used, for example, in the system of FIG. 6A.

A supercooling system was designed and fabricated consisting of PEF, OMF and real-time temperature, current and voltage measurement apparatus (FIG. 6A). A supercooling cube (1.5 inch by 1.5 inch by 1.5 inch), equipped with one pair of titanium plate electrodes in parallel, was assembled on the sample holder between a permanent magnet and electromagnet (FIG. 6B). For efficient cold air circulation, the supercooling cube was designed with plates having multiple holes. Magnetic forces were applied using a block of NdFeB permanent magnet (N52, Dx88-N52, K&J Magnetics, Inc., Jamison, Pa.; size: 2" by 2" by 1") and an electromagnet by alternating the charge and discharge to a magnet wire (22 AWG, EIS, Inc., Atlanta, Ga.) coiled to iron core (VIMVAR, Ed Fagan, Inc., Franklin Lakes, N.J.). The supercooling unit fabricated with electric and magnetic fields was placed in a commercial chest freezer (FCM7SUWW, GE, Inc., Fairfield, Conn.).

The oscillating magnetic field was generated by a pulse type of magnetic field with an intensity ranging from −150 mT to 150 mT. The applied voltage and pulse duty cycle was 30 V and 0.01, respectively and the applied frequency was 1 Hz. The combined magnetic flux densities by permanent magnet and electromagnet were oscillated between 50 to 150 mT per second at the center of the supercooling cube. The pulsed electric field was generated using an IGBT (IRAMX20UP60A. International Rectifier, El Segundo, Calif.) base power supply. Function generators (33220A, Agilent Technologies, Santa Clara, Calif.) were used to control the square wave forms with various duty cycles (D) and working frequencies. K-type thermocouple wire (PP-K-24S, Omega Engineering, Inc., Stamford, Conn.) aligned at the center of the cell and a data acquisition unit (DAQ. Agilent 39704A, Agilent Technologies, Inc., Palo Alto, Calif.) was used to monitor and collect he applied voltage and current, and temperature values of samples and air in a freezer. The data were scanned and transmitted at intervals of 1 second. The output signal was monitored in a digital oscilloscope (Model TDS2014; Tektronix, Beaverton, Oreg.) and the magnetic flux densities between two different magnets was measured using a handheld teslameter (4060.50 AE Teslameter, Frederikscn, Inc. Ølgod, Denmark). Freezer temperatures were controlled by a digital temperature controller (A419, Johnson Controls, Inc., Milwaukee, Wis.).

A cell was fabricated for measuring electrical conductivities of food samples. To measure electrical conductivities of supercooled chicken breasts, samples were placed and contacted between two electrodes in a freezer, operating at −7±0.5° C. Through the changes in electrical conductivities with temperature, the applied voltage and current were determined and tested for the desired cooling temperature profile. Acquired electrical conductivities of the samples were calculated by the following equation:

$$\sigma = \frac{LI}{AV}$$

Where L is the distance between two electrodes (m), A is the internal cross-sectional area (m$^2$), V is the applied voltage (V) and I is the measured electric current (A). From the obtained data, collected from 0° C. to the temperature where the phase transition begins, the electrical conductivities of tested food materials were plotted against temperature, and the temperature dependence of the measured electrical conductivity was depicted by a linear equation:

$$\sigma = \sigma_{ref} + mT$$

In order to generate a stair-shaped cooling rate, three different duty cycles. 0.2, 0.5 and 0.8 were used for the PEF treatment. The input voltage (5 $V_{p\text{-}p}$, peak-to-peak voltage) at a frequency of 20 kHz was set without electroconducting heating even at the maximum duty cycle (0.8); the maximum electric current was estimated to be 0.032 A. With the purpose to initiate the supercooling state in samples, the $V_{p\text{-}p}$ of 5 V with a duty cycle of 0.5 was applied to the samples until the electric current reached its minimum value in the supercooling state. The effects of PEF with duty cycle sequences of 0.8, 0.5, and 0.2 on the cooling rate of chicken breasts were explored. The applied periods for the duty cycle sequence were 300 sec, 120 sec, and 90 sec, respectively. To suppress ice nucleation, the OMF was applied only with PEF duty cycle of 0.2. Using this protocol, the stair-shaped cooling rate controls were repeated until the temperature of samples reached the freezer temperature, −7±0.5° C. Four experiments were carried out to validate the reproducibility.

Microstructure Analysis

The microstructures of chicken breast samples under different conditions (refrigeration at 4° C. (control-), freezing at −7° C. (control+), and supercooling by PEF and OMF combination at −7° C.) were studied using an inverted microscope (Leica-DMIL, Wetzlar, Germany), and changes in cell morphology were evaluated. The dissected chicken samples were frozen in isopentane at −80° C., and series of 10 µm-thick coronal sections were generated with a Leica CM 1900 cryostat (Leica Microsystems Buffalo Grove, Ill.). The structural change by both intra- and extracellular ice crystals was estimated by the cavity size observed in the meat cross-sectional area in the equivalent circular diameter.

Drip Loss

Drip has been used to describe exudates both from frozen thawed meat (drip) and from refrigerated or supercooled meat (weep). The drip loss was measured according to the method previously described by Ngapo et al. (1999. "Freezing and thawing rate effects on drip loss from samples of pork." *Meat Sci.* 53, 149-158), which is incorporated by reference herein for the limited purpose of disclosing a method for measuring drip loss. Fresh meat samples were measured within 30 min after the chicken breast was cut into chunks; drip loss of PEF and OMF treated and thawed samples were measured after refrigerated (0-4° C.) storage at 4 hours. Five samples were used for each combination of freezing, thawing and storage. The samples were cut into six cubes of approximately 0.5 inch length. Samples were suspended using nylon mesh and centrifuged at 40×g for 90 min. Drip loss was measured as:

$$Driploss(\%) = \frac{initial\,weight - final\,weight}{initial\,weight} \times 100$$

Color Measurement

To determine the whether treatments had any negative effects on the appearance of chicken breasts, instrumental color analysis was conducted. The Hunter L* (lightness), a* (redness-greenness), and b* (yellowness-blueness) values were measured using a color meter (ColorTec PCM, Clinton, N.J.). The net color difference (ΔE) was calculated with the equation:

$$\Delta E = \sqrt{(L_2^* - L_1^*)^2 + (a_2^* - a_1^*)^2 + (b_2^* - b_1^*)^2} \text{ where}$$

the subscripts 1 and 2 are referred to as color components before and after treatment, respectively.

Texture Analysis

After cooking in a 75° C. water bath for 30 min, texture was evaluated by shear force using a TA-XT2 texture analyzer (Stable Micro Systems, Godalming, UK) as described by Barbanti and Pasquini (2005, "Influence of cooking conditions on cooking loss and tenderness of raw and marinated chicken breast meat." *LWT—Food Sci. Technol.* 38, 895-901, herein incorporated by reference for the limited purpose of texture analysis method) with a slight modification. The operating parameters were with a 25 kg maximum cell load applied at a cross-head speed of 5 mm/s for 50% cutting distance. Results have been expressed as shear force (N of sample) and four measurements were performed on each sample.

pH Measurement

The pH value of chicken meat was determined using 5 g samples, homogenized with 5 ml of water. The pH was measured using a digital pH-meter (Mettler Toledo, Columbus, Ohio) with direct insertion of the probe electrode after calibration. Measurements of pH were calculated from the average of four replicates.

Lipid Oxidation Measurement

Thiobarbituric acid reactive substances (TBARS) indicate the oxidative changes in muscle foods during storage. The amounts of TBARS in raw chicken breast samples were determined in triplicates for each test using the procedure of McDonald and Hultin (1987) and Sayer and others (2001). Samples (1 g) were weighed in plastic bags (ZipLoc, SC Johnson, USA) and homogenized with 10 ml of deionized water. An aliquot of the sample (1 ml) was added to 2 ml of trichloroacetic acid/thiobarbituric acid (TCA/TBA), consisting of 15% TCA (w/v) and 0.375% TBA (w/v) in 0.25 M HCl and 3 ml of 2% butylated hydroxytoluene (BHT) (w/v) prepared in ethanol and mixed thoroughly. The mixture was vortexed and incubated for 15 min in 90° C. of water bath. The sample was cooled at room temperature for 10 min and centrifuged for 10 min at 1000×g. The absorbance of the resulting supernatant solution was determined at 532 nm on a visible spectrophotometer (Thermo Scientific GENE-SYS20, Thermo Fisher Scientific, Inc., Rochester, N.Y.). The TBARS values were calculated using a molar extinction coefficient of $1.56 \times 10^5$ $M^{-1}cm^{-1}$ and expressed as mg malondialdehyde (MDA) per kg of meat sample. For the measurement of lipid oxidation, four replicates were performed.

Statistical Analysis

The results of this study are presented as the means, standard errors and analysis of variance (ANOVA) routine to test the significance of the dissimilarities between the means of testing parameters among the treatments ($P < 0.05$).

1.2 Results

PEF and OMF Combination

Figure 7A:
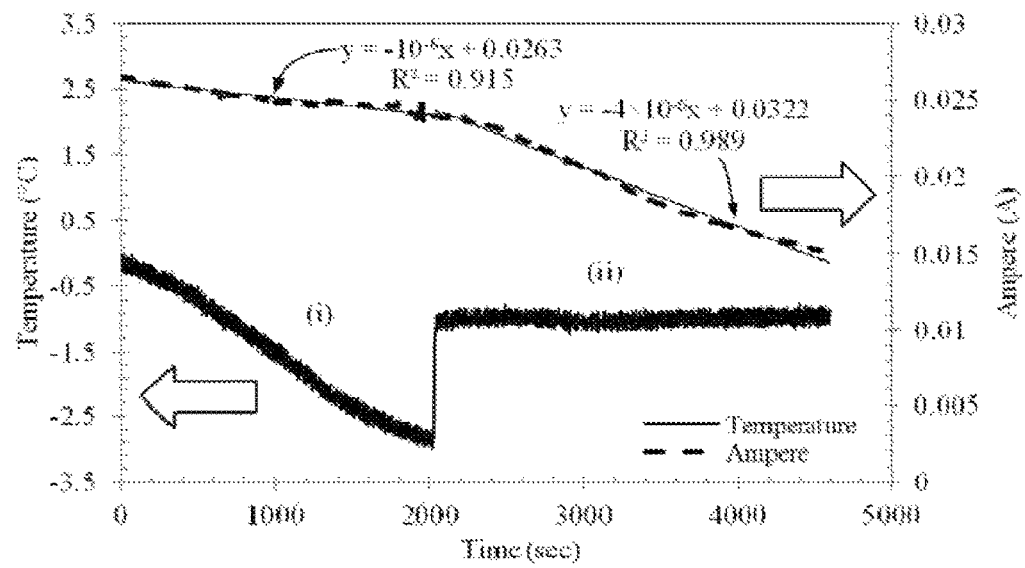
FIGS. 7A and 7B show the electrical properties of chicken breasts during the freezing process, consisting of (i) supercooling and (ii) phase transition.

Results from the measurement of electric current of raw chicken breasts demonstrated that its values were changing during the freezing process. The decreasing temperatures of samples triggered a decrease in the amount of flows of electric charge linearly (FIG. 7A). In addition, there was a deflection to the steeper linear trend around −3° C. Significant changes in the electric current values of chicken breast samples indicate ice nucleation inside of chicken breast samples. These observations were confirmed by the results of electrical conductivities changes in the function of temperature. Before ice nucleation occurred, a linear correlation was observed ($R^2 = 0.969$, FIG. 7(b)). In contrast, no significant correlation between electrical conductivities and temperature was demonstrated after nucleation.

Figure 7B:
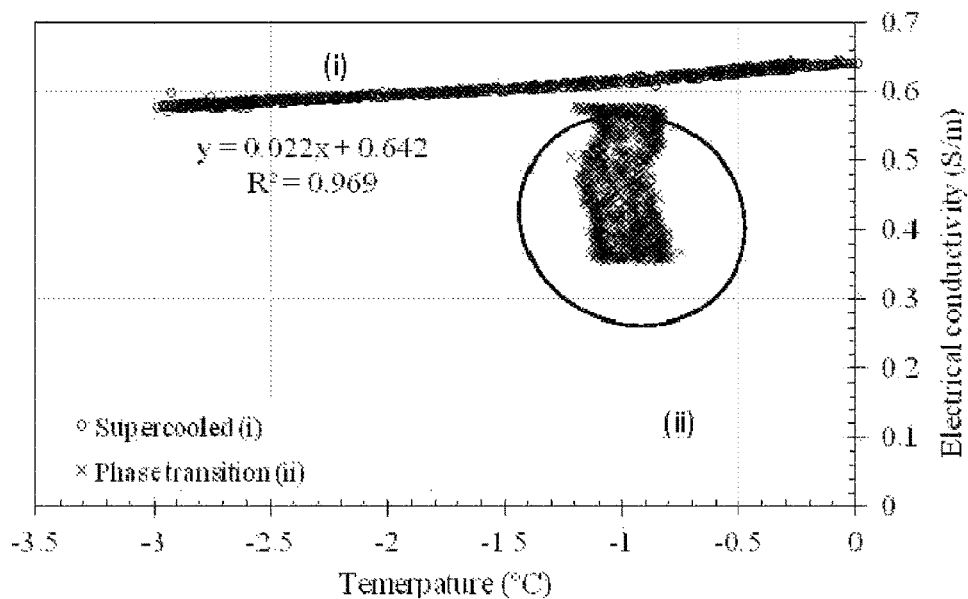

The electrical conductivities of the supercooling state in chicken samples are also given in FIG. 7B. The supercooling was found in the temperature range −1 to −3° C. before the sudden ice nucleation. The electrical conductivities of samples in the supercooling state presented high enough linear correlation ($R^2$=0.969) to be concluded as the same linear trend as the electrical conductivities of unfrozen state with the linear function of temperature. The decrease in electrical conductivities in the supercooling temperature range caused a decrease in the electric current of samples and minimum electrical conductivity and electric current in supercooled chicken breasts were estimated to 0.580 S/m and 0.024 A, respectively, before nucleation occurred.

Figure 8A:
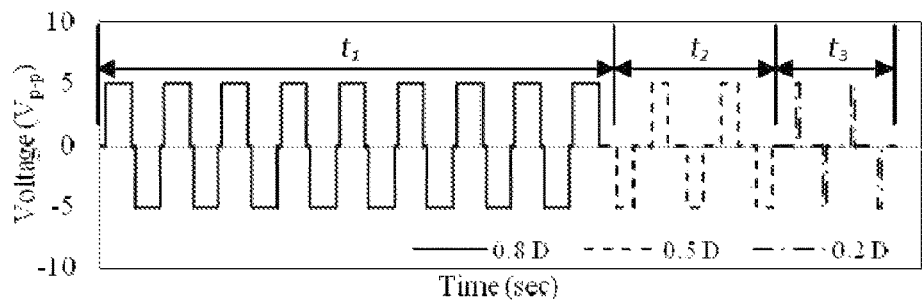
FIGS. 8A and 8B show the modification of the cooling rate of chicken breasts by strategically combined PEF and OMF treatments.

For full control of a stable supercooling, the stair-shaped cooling rates were designed using PEF with the sequence of three duty cycles (FIG. 8A). The PEF with duty cycles of 0.8, 0.5 and 0.2 was optimized to apply sequentially in different periods of 300, 120 and 90 seconds, respectively ($t_1$, $t_2$, and $t_3$, respectively, FIG. 8A).

Figure 8B:
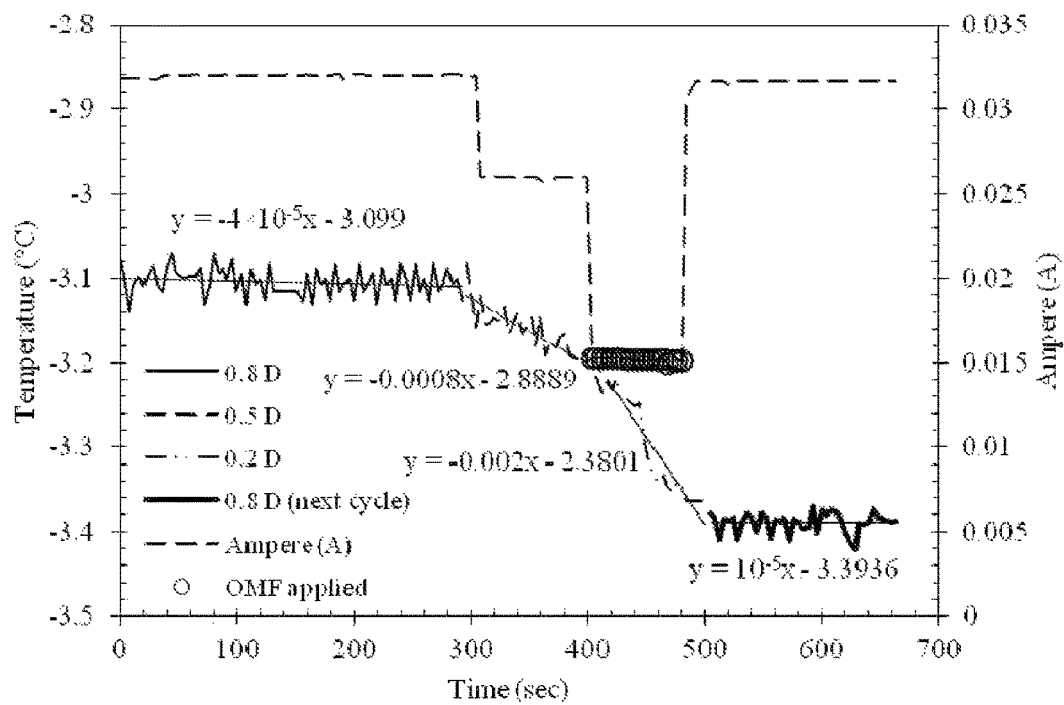

The temperature profiles of the PEF treatment under each of the different duty cycle is shown in FIG. 8B. It can be seen that maximum duty cycle of 0.8 resulted in the constant sample temperature. The decrease in duty cycles evoked an increase in cooling rates of chicken breast samples up to −0.12° C./min. This indicates is that the duty cycle sequence brings about the modification of cooling rates which leads to a stair-shaped temperature profile.

The combination of PEF and OMF thus successfully prevented ice nucleation without any noticeable electrical interference (FIG. 8B).

Effects of Developed PEF and OMF Combination on Extension of Supercooling

Figure 9:
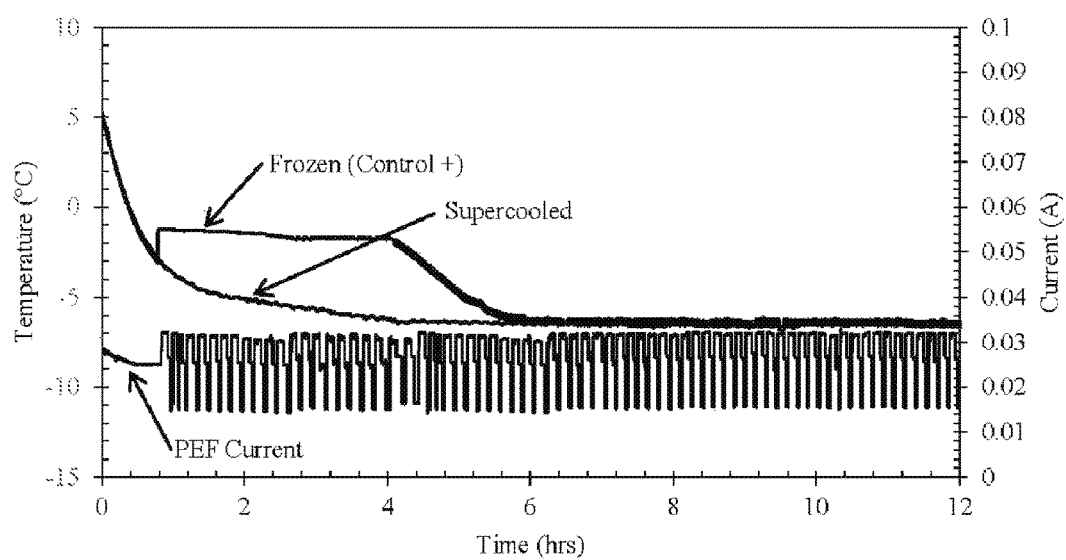
FIG. 9 displays the temperature profiles of chicken breasts stored at −7±0.5° C. The control was fully frozen and reached a temperature of −6.5° C. Samples undergoing the combined PEF and OMF treatments stayed in the supercooling state during the entire testing period.

FIG. 9 shows the temperature as a function of time under the combined PEF and OMF treatments using developed protocol. For comparison of the proposed PEF and OMF treatment protocol, the chicken breasts without any treatments were employed as a control. The same cooling rates can be seen for controls and the combined PEF and OMF treated samples before the controls became frozen. During this period, the effect of the combined PEF and OMF treatment diverged from the control when the electric current reached its minimum upon reaching the supercooling state (0.024 A). Therefore, it can be concluded that the developed PEF and OMF treatment are based on the interaction of water molecules rather than thermal effect.

The PEF and OMF treated samples remained in the supercooling state (no ice nucleation), while the controls were fully frozen. Since there is no freezing point on the chicken samples under PEF and OMF combination, the degree of supercooling of PEF and OMF treated chicken samples was estimated by the temperature difference between the freezer temperature and freezing point for the controls. The mean degree of supercooling of chicken breasts under PEF and OMF treatment was 5.6±0.2° C., as compared with 1.6±1.4° C. for the controls. In all cases, there was no sudden ice nucleation to the samples under the developed PEF and OMF treatment. Therefore, the control strategy using developed PEF and OMF combination was effective and applicable to maintaining the supercooling state in chicken breast samples.

Figure 10A:
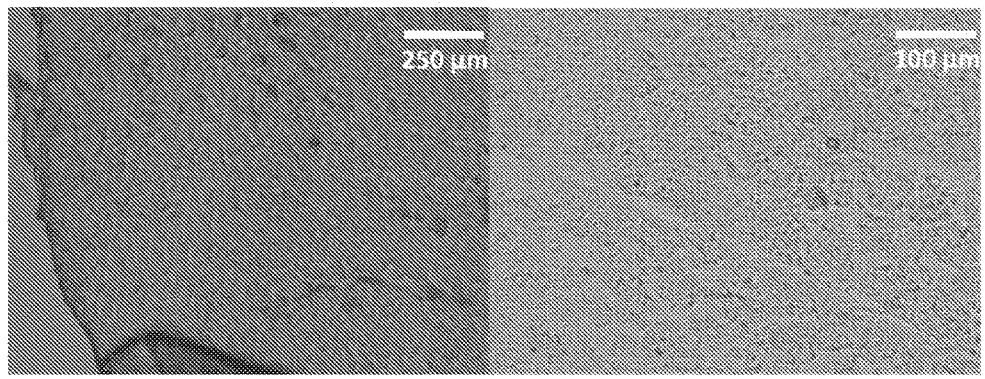
FIGS. 10A-C show micrographs of chicken breast samples under different storage conditions.
Figure 10B:
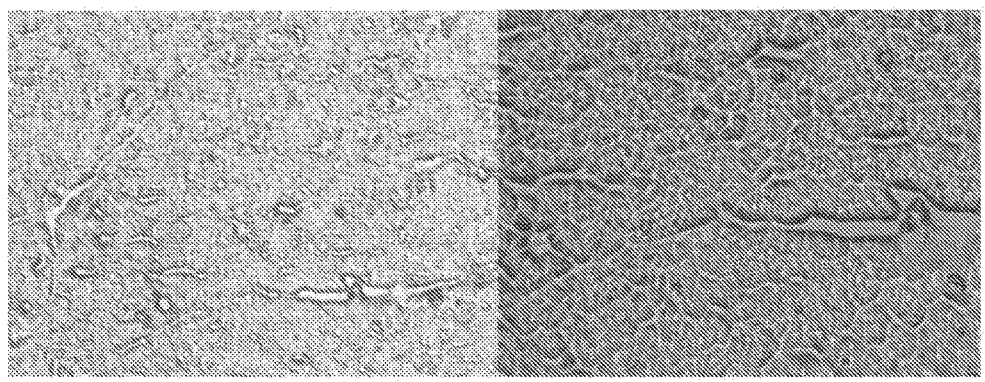
Figure 10C:
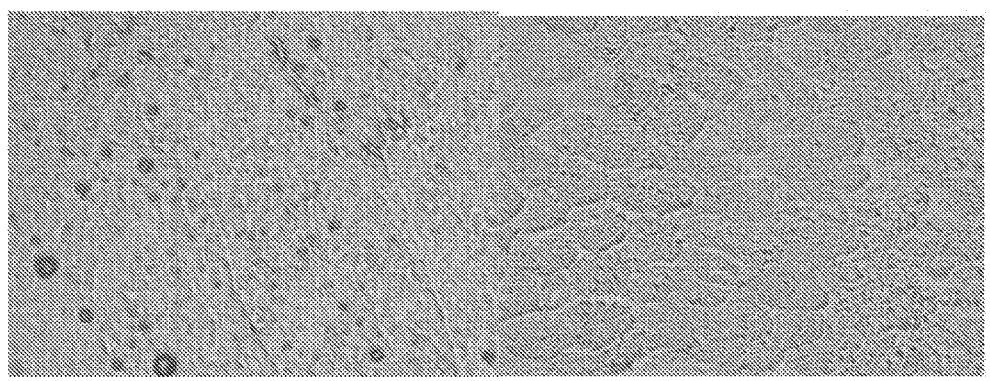

Effects of Developed PEF and OMF Combination on the Microstructure of Chicken Breasts The structures of sample tissues in the supercooling state were illustrated by optical microscopy and micrographs of representative images of chicken breasts after different treatments are shown in FIG. 10A-C. The micrograph images show that the refrigerated meats maintained their compact fiber tissues and no voids were observed between tissues. On the other hand, when the samples were frozen, the ice crystals were evident by some voids and distortion of tissues. Even after short terms in the frozen state, the fully frozen samples displayed significant damages. The equivalent circular diameters of cavities were estimated to 204±70 μm. Note that the cavity sizes vary in whole cross-sectional area and a large number of freeze-cracks were proceeded. The micrographs corresponding to meat in supercooling (FIG. 10C) show no noticeable structural damage and cell disruption similar to the condition displayed by the refrigerated (unfrozen) sample.

Effects of PEF and OMF Combination on the Qualities of Supercooled Chicken Breasts Quality parameters, including drip loss, color, texture, pH and lipid oxidation, were measured to assess the quality changes on supercooled chicken breast samples. In comparison to the quality factors, the quality values of initial chicken breast samples at 4° C. were considered as controls. Table 1 shows that the quality parameter changes after different cold temperature storage conditions: fresh, refrigerated at 4° C. for 12 hours, frozen and supercooled at −7° C. for 12 hours.

TABLE 1

Mean values (±S.D.) of physical and chemical changes over initial (at 4° C., Control), refrigerated (at 4° C. for 12 hours, Control−), frozen (at −7° C. for 12 hours and thawed at 4° C. for 4 hours, respectively, Control+), and supercooled (at −7° C. for 12 hours) chicken breast samples

| Parameter | Initial | Refrigerated | Frozen | Supercooled |
|---|---|---|---|---|
| Drip loss (%) | 0.83 ± 0.14$^a$ | 0.85 ± 0.06$^a$ | 1.74 ± 0.17$^b$ | 0.79 ± 0.10$^a$ |
| Color change (ΔE) | N/A | 0.35 ± 0.03$^a$ | 0.32 ± 0.02$^a$ | 0.33 ± 0.04$^a$ |
| Texture (N) | 27.24 ± 1.68$^{a,b}$ | 26.77 ± 1.25$^a$ | 25.67 ± 1.44$^c$ | 27.30 ± 1.36$^b$ |
| pH | 6.40 ± 0.01$^a$ | 6.41 ± 0.01$^a$ | 6.40 ± 0.02$^a$ | 6.40 ± 0.01$^a$ |
| TBARS (mg MDA/kg meat) | 0.26 ± 0.03$^{a,b}$ | 0.29 ± 0.02$^b$ | 0.26 ± 0.01$^a$ | 0.26 ± 0.01$^a$ |

In each row, dissimilar small letters in each cell indicate a significant difference at 0.05 levels.

Regarding drip loss, the values were not significantly different for fresh, refrigerated and supercooled chicken breasts. The chicken breasts frozen at −7° C. showed an increase in drip loss which indicates myofibrillar shrinkage and muscle cell damages by the formation of ice crystals. The microstructure of breast meat after frozen storage was shown in FIG. 10B, and confirms that ice crystal growth during freezing storage was such that major structural damage occurred in the muscle fibers. Therefore, the degree of loss in water holding capacity would be or become similar to the trends that could be observed from the drip loss.

The shear force results show that the tenderness of frozen chicken breasts decreased significantly (P<0.05). The underlying mechanism in the loss of tenderness is also derived from the breakdown of the muscle fibers and the loss of structural integrity caused by ice crystal formation. The formation of extracellular ice crystals disrupts the physical structure, largely breaking myofibrils apart and resulting in loss of tenderness. In contrast, both the refrigerated and supercooled chicken breasts were as tender as original samples (P>0.05).

The measurements of TBARS in chicken samples demonstrated the amount of secondary oxidation product, malondialdehyde (MDA). The TBARS value of refrigerated chicken breasts was significantly higher than stored in other conditions. The inhibition of TBARS was estimated at most to be 20% by freezing or supercooling as compared to refrigeration and it indicates that subzero temperature storage was effective in reducing lipid oxidation of chicken breasts.

From the foregoing tests, the supercooled chicken breast samples maintained the original qualities of a fresh chicken product. Overall, the findings of the current study demonstrate that the strategy of PEF and OMF combination for prolonging the supercooled state is applicable to maintain the original qualities while achieving satisfactory long term storage of perishable materials.

Example 2

Storage of Meat Products in the Supercooled State

Figure 11:
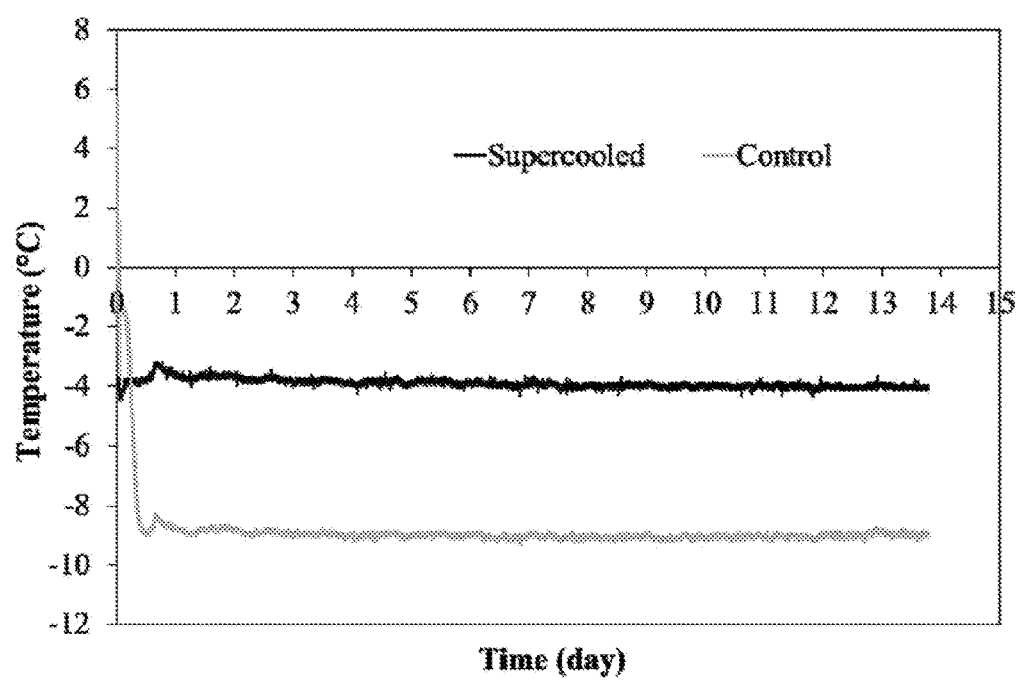
FIG. 11 shows temperature profiles of supercooled beef at −4° C. for two weeks. A control beef sample without the application of both of the PEF and OMF was frozen in 2 hours.

A meat product selected from chicken, beef, pork, fish, or another animal was placed into the cooling compartment of an apparatus as described herein. The apparatus was subsequently transferred to a freezer which had an internal temperature controlled at about −8° C. Upon placement in the freezer, the combined application of PEF and OMF was initiated. The programmed duty cycles for the PEF and OMF continued to repeat during the cooling process and throughout the storage period. The meat product was stored in the resulting supercooled state for about two weeks (FIG. 11). The meat product was preserved such that there was no significant change in color, drip loss or tenderness relative to fresh meat.

Example 3

Storage of a Biological Organ in the Supercooled State

A biological organ is placed into the cooling compartment of an apparatus as described herein. The apparatus is subsequently transferred to a freezer which has an internal temperature controlled at about 0° C. to about −20° C. such as about −7° C. Upon placement in the freezer, the apparatus is used to apply combined PEF and OMF to the organ such that it is maintained in a supercooled state. The biological organ is stored in the resulting supercooled state and has no significant change in structure or function as a result of the supercooling process.

What is claimed is:

1. A method of supercooling a perishable product in a container comprising the steps of:
    cooling the perishable product to a temperature within the range of about 0° C. to about −20° C. while applying an oscillating magnetic field to the perishable product; and
    simultaneously applying the oscillating magnetic field and a pulsed electric field to the cooled perishable product while maintaining the temperature below the freezing point of the perishable product, wherein the pulsed electric field is applied through a pair of electrodes directly in contact with the perishable product.

2. The method of claim 1, wherein the perishable product is a food product.

3. The method of claim 2, wherein the food product is a meat product.

4. The method of claim 1, wherein the perishable product is an organ or body tissue.

5. The method of claim 1, wherein the perishable product is cooled to a temperature within the range of about −4° C. to about −7° C.

6. The method of claim 1, wherein the pulsed electric field is provided as a pulsed squared waveform.

7. The method of claim 6, wherein the squared waveform is provided at a frequency of at least 20 kHz.

8. The method of claim 1, wherein the oscillating magnetic field has a strength of about 50 to 500 mT as measured at the center of the container.

9. The method of claim 1, wherein no ice crystals are formed within the supercooled perishable product.

10. The method of claim 1, additionally comprising applying the pulsed electric field to the perishable product during cooling.

11. The method of claim 1, wherein the perishable product is selected from food products, organs, tissues, biologics, cell cultures, stem cells, embryos, blood, reactive solutions, and unstable chemical reagents.

12. A method of preserving a food product at a temperature below its freezing point comprising:
    cooling the food product to a temperature below its freezing point while applying an oscillating magnetic field to the food product; and
    maintaining the food product below its freezing point for a desired period of time while applying the oscillating magnetic field and applying a pulsed electric field through electrodes contacting the food product.

13. The method of claim 12, wherein the food product comprises one or more pieces of meat.

14. The method of claim 13, wherein the meat is one or more of chicken, beef and fish.

15. The method of claim 12, wherein the food product is a vegetable.

16. The method of claim 12, wherein the food product is preserved for more than 24 hours.

17. The method of claim 16, wherein there is no significant change in one or more of the color, drip loss or tenderness of the food product relative to a food product that was not preserved.

18. The method of claim 12, additionally comprising applying a pulsed electric field to the food product during the cooling.

19. The method of claim 12, wherein the pulsed electric field is provided as a squared waveform.

20. The method of claim 19, wherein the squared waveform is provided with a duty cycle of about 0.2 to about 0.8.

21. The method of claim 19, wherein the squared waveform is provided with more than one duty cycle.

22. The method of claim 21, wherein the square waveform is provided with duty cycles of 0.2, 0.5 and 0.8.

23. The method of claim 12, wherein the oscillating magnetic field has a strength of about 50 to 500 mT.

24. A method of preserving an organ comprising cooling the organ to below 0° C. while applying an oscillating magnetic field to the organ and subsequently applying a pulsed electric field and the oscillating magnetic field to the organ, wherein the pulsed electric field is applied through two contact electrodes.

25. The method of claim 24, wherein the pulsed electric field is provided as a pulsed square waveform.

26. The method of claim 24, wherein the oscillating magnetic field has a strength of about 50 to 500 mT.

27. The method of claim 24, wherein the organ is maintained at the temperature below 0° C. for more than 24 hours while continuing to apply the pulsed electric field and oscillating magnetic field.

28. The method of claim 1, wherein the pulsed electric field has a strength of about 0.6 V/cm to about 10 V/cm.

29. The method of claim 12, wherein the pulsed electric field has a strength of about 0.6 V/cm to about 10 V/cm.

30. The method of claim 24, wherein the pulsed electric field has a strength of about 0.6 V/cm to about 10 V/cm.

\* \* \* \* \*